US00PP30692P2

(12) United States Plant Patent
Ruigrok

(10) Patent No.: US PP30,692 P2
(45) Date of Patent: Jul. 9, 2019

(54) ***DAHLIA* PLANT NAMED 'BKDAMAGFR'**

(50) Latin Name: *Dahlia hybrida*
Varietal Denomination: BKDAMAGFR

(71) Applicant: Sanne Helena Ruigrok, Hillegom (NL)

(72) Inventor: Sanne Helena Ruigrok, Hillegom (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/932,676

(22) Filed: Apr. 6, 2018

(51) Int. Cl.
*A01H 5/02* (2018.01)

(52) U.S. Cl.
USPC ..... Plt./321

(58) Field of Classification Search
USPC ..... Plt./321
See application file for complete search history.

*Primary Examiner* — Annette H Para
(74) *Attorney, Agent, or Firm* — C. A. Whealy

(57) ABSTRACT

A new and distinct cultivar of *Dahlia* plant named 'BKDAMAGFR', characterized by its broadly upright plant habit; moderate basal branching habit; dense and bushy growth habit; dark green-colored leaves; and large cactus type inflorescences with yellow and red bi-colored ray florets.

2 Drawing Sheets

Botanical designation: *Dahlia hybrida.*
Cultivar denomination: 'BKDAMAGFR'.

BACKGROUND OF THE INVENTION

The present invention relates to a new and distinct cultivar of *Dahlia* plant, botanically known as *Dahlia hybrida* and hereinafter referred to by the name 'BKDAMAGFR'.

The new *Dahlia* plant is a product of a planned breeding program conducted by the Inventor in Hillegom, The Netherlands. The objective of the breeding program is to create new large container *Dahlia* plants with large and attractive cactus type inflorescences.

The new *Dahlia* plant originated from a cross-pollination in September, 2013 in Hillegom, The Netherlands of a proprietary selection of *Dahlia hybrida* identified as code number FET.S12.014.015, not patented, as the female, or seed, parent with a proprietary selection of *Dahlia hybrida* identified as code number FET.S12.006.004, not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in October, 2015.

Asexual reproduction of the new *Dahlia* plant by vegetative terminal cuttings in a controlled greenhouse environment in Maasdijk, The Netherlands since February, 2016 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMAGFR'. These characteristics in combination distinguish 'BKDAMAGFR' as a new and distinct *Dahlia* plant:

1. Broadly upright plant habit.
2. Moderate basal branching habit; dense and bushy growth habit.
3. Dark green-colored leaves.
4. Large cactus type inflorescences with yellow and red bi-colored ray florets.

Plants of the new *Dahlia* differ primarily from plants of the female parent selection in the following characteristics:

1. Plants of the new *Dahlia* are taller than plants of the female parent selection.
2. Plants of the new *Dahlia* and the female parent selection differ in ray floret color as plants of the female parent selection have red-colored ray florets.

Plants of the new *Dahlia* differ primarily from plants of the male parent selection in the following characteristics:

1. Plants of the new *Dahlia* are shorter than plants of the male parent selection.
2. Plants of the new *Dahlia* have shorter internodes than plants of the male parent selection.
3. Plants of the new *Dahlia* and the male parent selection differ in ray floret color as plants of the male parent selection have orange yellow-colored ray florets.

Plants of the new *Dahlia* can be compared to plants of *Dahlia hybrida* 'XXL Sunset', not patented. In side-by-side comparisons, plants of the new *Dahlia* differ from plants of 'XXL Sunset' in the following characteristics:

1. Inflorescences of plants of the new *Dahlia* are cactus types whereas inflorescences of plants of 'XXL Sunset' are semi-cactus types.
2. Plants of the new *Dahlia* and 'XXL Sunset' differ in ray floret color as plants of 'XXL Sunset' have salmon and yellow bi-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAMAGFR' grown in a container.

The photograph on the second sheet is a close-up view of a typical flowering plant of 'BKDAMAGFR'.

DETAILED BOTANICAL DESCRIPTION

The aforementioned photographs and the following observations and measurements describe plants grown during the winter in 19-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks old when the photographs and description were taken. To induce inflorescence initiation and development, plants were grown under short nyctoperiod (long day) conditions. In the following description, color references are made to The Royal Horticultural Society Colour Chart, 2015 Edition, except where general terms of ordinary dictionary significance are used.

Botanical classification: *Dahlia hybrida* 'BKDAMAGFR'.

Parentage:

- *Female, or seed, parent*.—Proprietary selection of *Dahlia hybrida* identified as code number FET.S12.014.015, not patented.
- *Male, or pollen, parent*.—Proprietary selection of *Dahlia hybrida* identified as code number FET.S12.006.004, not patented.

Propagation:

- *Type*.—By vegetative terminal cuttings.
- *Time to initiate roots, summer*.—About 16 days at temperatures ranging from 18° C. to 21° C.
- *Time to initiate roots, winter*.—About 19 days at temperatures ranging from 19° C. to 21° C.
- *Time to produce a rooted young plant, summer*.—About 23 days at temperatures ranging from 18° C. to 21° C.
- *Time to produce a rooted young plant, winter*.—About 25 days at temperatures ranging from 19° C. to 21° C.
- *Root description*.—Medium in thickness, fibrous; typically white in color, actual color of the roots is dependent on substrate composition, water quality, fertilizers, substrate temperature and physiological age of roots; tuber development has not been observed on plants of the new *Dahlia*.
- *Rooting habit*.—Moderately freely branching; medium density.

Plant description:

- *Plant and growth habit*.—Broadly upright and mounding plant form; overall plant shape, flattened globular; moderate basal branching habit with about five primary branches each with about three secondary branches developing per plant; inflorescences held above and beyond the foliar plane on strong peduncles; bushy and dense growth habit; pinching is not required but will improve branching habit; moderately vigorous growth habit.
- *Plant height, soil level to top of foliar plane*.—About 19.8 cm.
- *Plant height, soil level to top of floral plane*.—About 25.8 cm.
- *Plant diameter or spread*.—About 32.5 cm.
- *Lateral branches*.—Length: About 12.4 cm. Diameter: About 6 mm. Internode length: About 3.2 cm. Aspect: Primary branches are about 45° from vertical; secondary branches, about 50° from primary branch axis. Strength: Moderately strong. Texture and luster: Smooth, glabrous; glossy. Color, developing: Close to 143C. Color, developed: Close to 144A.

Leaf & leaflet description:

- *Arrangement*.—Leaves opposite and simple or compound with three or five leaflets.
- *Length, simple leaves*.—About 10 cm.
- *Length, compound leaves*.—About 13.5 cm.
- *Length, terminal leaflets*.—About 11.3 cm.
- *Length, lateral leaflets*.—About 8.3 cm.
- *Width, simple leaves*.—About 6.1 cm.
- *Width, compound leaves*.—About 12.8 cm.
- *Width, terminal leaflets*.—About 4.9 cm.
- *Width, lateral leaflets*.—About 3.7 cm.
- *Shape, simple leaves*.—Ovate.
- *Shape, compound leaves in overall outline*.—Ovate.
- *Shape, leaflets*.—Ovate.
- *Apex, leaves and leaflets*.—Apiculate.
- *Base, leaves and leaflets*.—Attenuate.
- *Margin, leaves and leaflets*.—Coarsely serrate.
- *Venation pattern, leaves and leaflets*.—Pinnate.
- *Texture and luster, upper surface, leaves and leaflets*.—Smooth, moderately pubescent; slightly velvety; slightly glossy.
- *Texture and luster, lower surface, leaves and leaflets*.—Smooth, moderately pubescent; matte.
- *Color*.—Developing leaves and leaflets, upper surface: Close to between 141A and 143A. Developing leaves and leaflets, lower surface: Close to 138A to 138B. Fully expanded leaves and leaflets, upper surface: Close to between NN137A and 147A; venation, close to 144A. Fully expanded leaves and leaflets, lower surface: Close to 191A; venation, close to 146B.
- *Petioles, leaves and leaflets*.—Length: About 3.3 cm. Diameter: About 3.5 mm. Strength: Moderately strong. Texture and luster, upper and lower surfaces: Smooth, glabrous; glossy. Color, upper and lower surfaces: Close to 146B.

Inflorescence description:

- *Appearance and arrangement*.—Large cactus type inflorescences with ray and disc florets forming acropetally on a receptacle; inflorescences positioned above and beyond the foliar plane on strong peduncles; inflorescences face mostly upright to slightly outwardly; freely flowering habit with about 35 inflorescences develop per plant.
- *Fragrance*.—None detected.
- *Flowering response and flowering period*.—Early flowering habit, plants begin flowering about 41 days after planting; plants flower continuously during the autumn into the winter in The Netherlands.
- *Post-production longevity*.—Inflorescences maintain good substance for about ten days on the plant; inflorescences persistent.

*Inflorescence buds*.—Height: About 1.7 cm. Diameter: About 1.2 cm. Shape: Ovoid. Texture and luster: Smooth, glabrous; glossy. Color: Close to 144B; towards the base, close to 144A and towards the apex, close to 182D.

*Inflorescence size*.—Diameter: About 9.8 cm. Depth (height): About 6.1 cm. Disc diameter: About 9 mm, typically inconspicuous.

*Receptacles*.—Height: About 4 mm. Diameter: About 3 mm. Shape: Pyramidal. Color: Close to 145B.

*Ray florets*.—Quantity per inflorescence and arrangement: About 120 arranged in about six whorls. Length: About 4.7 cm. Width: About 1.3 cm. Shape: Oblanceolate. Apex: Acute. Base: Attenuate. Margin: Entire; distally, strongly revolute. Aspect: Varying from −35° to 40° from horizontal; strongly convex. Texture and luster, upper surface: Smooth, glabrous; velvety; matte. Texture and luster, lower surface: Smooth, glabrous; slightly velvety; slightly glossy. Color: When opening, upper surface: Close to 1A to 1B; towards the apex, close to 42B. When opening, lower surface: Close to 1C to 1D; fading towards the apex to close to 35C. Fully opened, upper surface: Close to 1A to 1B; towards the apex, close to 53A; venation, similar to lamina colors; colors do not change with development. Fully opened, lower surface: Close to 2C; fading towards the apex to close to 54C; venation, similar to lamina colors; colors do not change with development.

*Disc florets*.—Quantity per inflorescence and arrangement: About ten massed at the center of the inflorescence in about two spiral whorls; typically inconspicuous. Length: About 1.4 cm. Diameter: About 7 mm. Shape: Tubular, elongated; apices, acute. Texture and luster, inner and outer surfaces: Smooth, glabrous; glossy. Color, when opening, inner and outer surfaces: Close to 14A to 14B; towards the base, close to 145D. Color, fully opened, inner and outer surfaces: Close to 154B to 154C; towards the base, close to 145D.

*Phyllaries*.—Quantity per inflorescence and arrangement: About six arranged in a single whorl. Length: About 1.3 cm. Width: About 4 mm. Shape: Narrowly ovate. Apex: Acute. Base: Cuneate. Margin: Entire. Texture and luster, upper and lower surfaces: Smooth, glabrous; moderately glossy. Color, upper and lower surfaces: Close to NN137B.

*Ray floret bracts*.—Quantity per inflorescence and arrangement: One subtending each ray floret. Length: About 1.9 cm. Width: About 6 mm. Shape: Ovate. Apex: Acute. Base: Broadly cuneate. Margin: Entire. Texture and luster, upper and lower surfaces: Smooth, glabrous; glossy. Color, upper and lower surfaces: Close to N144A; towards the base, close to 144B.

*Peduncles*.—Length, terminal peduncle: About 9 cm. Diameter, terminal peduncle: About 3 mm. Strength: Strong. Texture and luster: Smooth, glabrous; moderately glossy. Color: Close to 152A.

*Reproductive organs*.—Androecium, present on disc florets only: Quantity per floret: About five. Filament length: About 2 mm. Filament color: Close to 150D. Anther shape: Narrowly oblong. Anther length: About 4 mm. Anther color: Close to 13A to 13B. Pollen amount: Moderate. Pollen color: Close to 21A. Gynoecium, present on disc florets only: Quantity per floret: One. Pistil length: About 1 cm. Style length: About 2 mm. Style color: Close to 154C. Stigma diameter: About 6 mm. Stigma shape: Cleft. Stigma color: Close to 21B. Ovary color: Close to 145C. Seeds and fruits: Seed and fruit development have not been observed on plants of the new *Dahlia* to date.

Disease & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAM-AGFR' as illustrated and described.

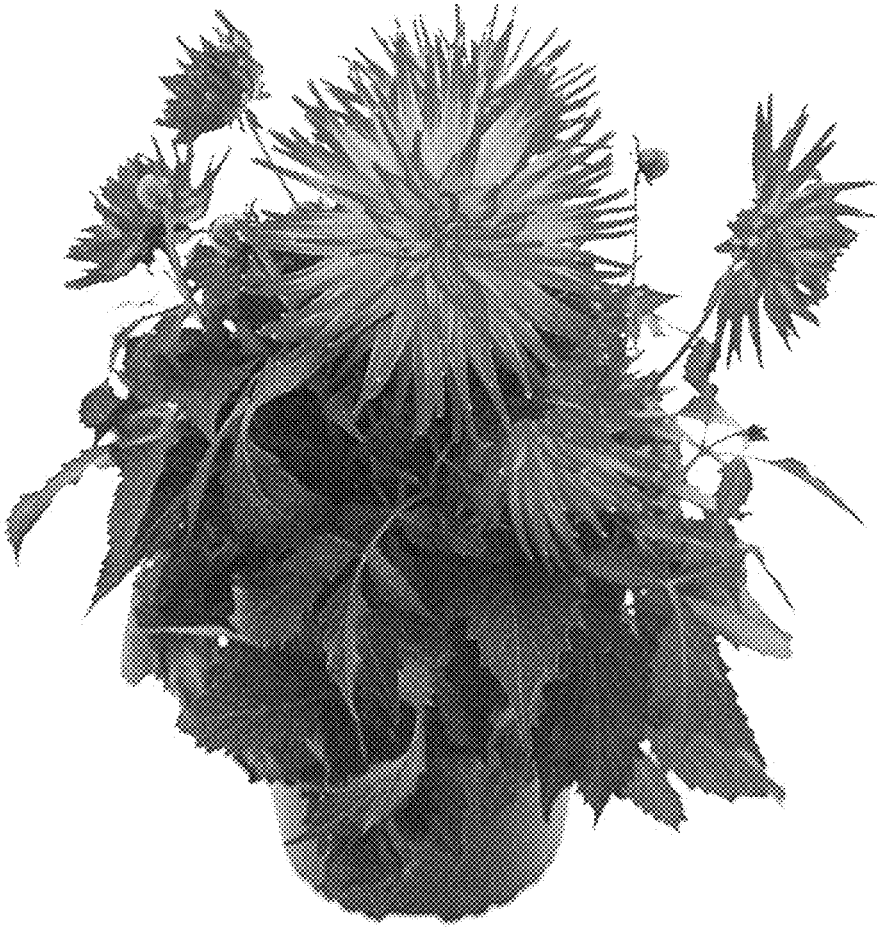

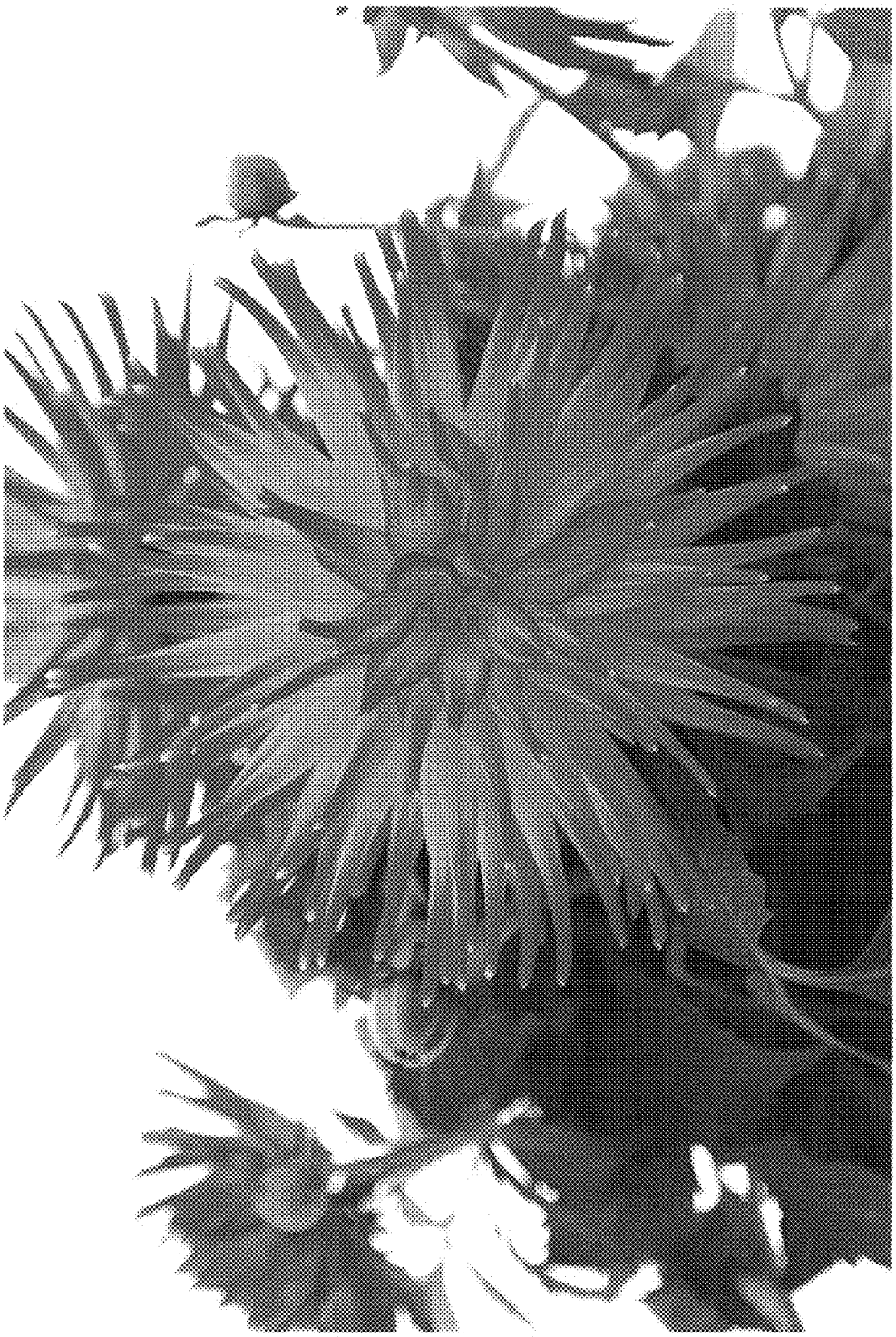

* * * * *